United States Patent [19]
Richter et al.

[11] 3,950,307
[45] Apr. 13, 1976

[54] HALOBENZOYL TETRAHALOPHTHALIMIDES
[75] Inventors: Sidney B. Richter, Chicago; Glendon D. Kyker, Glen Ellyn, both of Ill.
[73] Assignee: Velsicol Chemical Corporation, Chicago, Ill.
[22] Filed: Mar. 10, 1975
[21] Appl. No.: 554,895

[52] U.S. Cl... 260/45.75 B; 260/45.8 N; 260/326 A
[51] Int. Cl.$^2$ C07D 209/48; C08L 23/00; C08L 25/06
[58] Field of Search..... 260/326 A, 45.8 N, 45.75 B

[56] References Cited
FOREIGN PATENTS OR APPLICATIONS
4,727,138   7/1972   Japan .......................... 260/326 HL

*Primary Examiner*—Lewis Gotts
*Assistant Examiner*—S. P. Williams
*Attorney, Agent, or Firm*—Robert J. Schwarz; Dietmar H. Olesch

[57] ABSTRACT

This invention discloses fire retardant chemical compounds of the formula

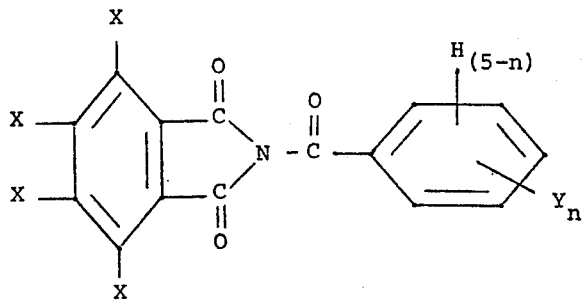

wherein X and Y are each chlorine or bromine and n is an integer from 2 to 5 which are useful in polymeric compositions.

13 Claims, No Drawings

HALOBENZOYL TETRAHALOPHTHALIMIDES

This invention relates to new compositions of matter and more specifically relates to new chemical compounds of the formula:

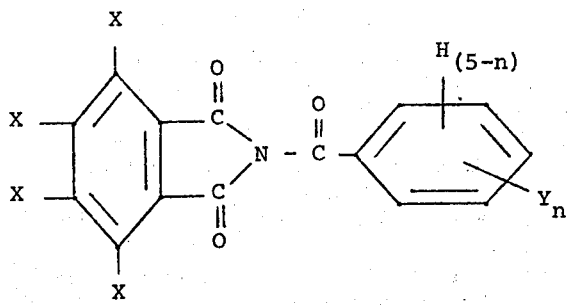

(I)

wherein X and Y are each chlorine or bromine and $n$ is an integer from 2 to 5.

The compounds of the present invention possess exceptional properties in rendering combustible polymers fire retardant when intimately admixed therewith.

The compounds of the present invention can be conveniently prepared by reacting a compound of the formula

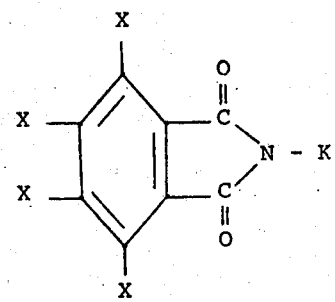

(II)

wherein X is as heretofore described, with an about equimolar amount of a benzoyl chloride of the formula

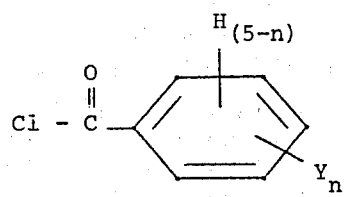

(III)

wherein Y and $n$ are as heretofore described. This reaction can be effected by incrementally adding the benzoyl chloride of formula III to a slurry or solution of the compound of formula II in an inert organic reaction medium such as dioxane. After the addition is completed the reaction mixture can be heated at reflux for a period of from ½ to about 4 hours to ensure completion of the reaction. After this time the reaction mixture can be filtered and the filtrate stripped of solvent to yield the desired product as the residue. This product can be used as such or can be further purified by conventional techniques well known in the art.

The compounds of formula II, consisting of 3,4,5,6-tetrachlorophthalimide and 3,4,5,6-tetrabromophthalimide, when not readily available can be conveniently prepared from the corresponding tetrahalophthalic anhydride by reaction with concentrated ammonium hydroxide. This reaction can be effected by slowly adding the ammonium hydroxide, with stirring, at room temperature. After the addition is completed, the reaction mixture can be heated with continued stirring for a period sufficient to evaporate the water present. The remaining solid product can then be further dried in a forced air oven and can thereafter be used as such or can be further purified by conventional means such as recrystallization.

The compounds of formula II are the potassium salt of 3,4,5,6-tetrabromophthalimide and the potassium salt of 3,4,5,6-tetrachlorophthalimide, whereas exemplary compounds of formula III are 2,4-dichlorobenzoyl chloride, 2,5-dichlorobenzoyl chloride, 2,6-dichlorobenzoyl chloride, 3,4-dichlorobenzoyl chloride, 3,5-dichlorobenzoyl chloride, 2,4-dibromobenzoyl chloride, 2,5-dibromobenzoyl chloride, 2,6-dibromobenzoyl chloride, 3,4-dibromobenzoyl chloride, 3,5-dibromobenzoyl chloride, 2,3,4-trichlorobenzoyl chloride, 2,3,5-trichlorobenzoyl chloride, 2,4,5-trichlorobenzoyl chloride, 2,4,6-trichlorobenzoyl chloride, 3,4,5-trichlorobenzoyl chloride, 2,3,4-tribromobenzoyl chloride, 2,3,5-tribromobenzoyl chloride, 2,4,5-tribromobnezoyl chloride, 2,4,6-tribromobenzoyl chloride, 3,4,5-tribromobenzoyl chloride, 2,3,4,5-tetrachlorobenzoyl chloride, 2,3,5,6-tetrachlorobenzoyl chloride, 2,3,4,6-tetrachlorobenzoyl chloride, 2,3,4,5-tetrabromobenzoyl chloride, 2,3,5,6-tetrabromobenzoyl chloride, 2,3,4,6-tetrabromobenzoyl chloride, pentachlorobenzoyl chloride, pentabromobenzoyl chloride and the like.

The manner in which the compounds of this invention can be prepared is more specifically illustrated in the following examples.

EXAMPLE 1

Preparation of 3,4,5,6-Tetrabromophthalimide 3,4,5,6-Tetrabromophthalic anhydride (100 grams; 0.217 mole) was charged into a glass reaction vessel. Concentrated ammonium hydroxide (300 ml) was incrementally added at room temperature with stirring. After the addition was completed the reaction slurry was heated with stirring for a period of about 2 hours resulting in the evaporation of most of the water present and leaving a yellow powder. The powder was further dried in a forced air oven and was then recrystallized from benzyl alcohol. The crystalline product was then washed with acetone, filtered and dried to yield the desired product 3,4,5,6-tetrabromophthalimide.

EXAMPLE 2

Preparation of the Potassium Salt of 3,4,5,6-Tetrabromophthalimide

Anhydrous dioxane (2000 ml) was charged into a glass reaction vessel equipped with a mechanical stirrer and thermometer. The dioxane was heated to a temperature of from 90° to 99°C and 3,4,5,6-tetrabromophthalimide (75 grams) was incrementally added with stirring. Potassium hydroxide (0.162 moles) dissolved in methanol was added to the reaction mixture with heating and stirring. The reaction mixture was cooled and a small amount of phenolphthalein indicator was added thereto. Additional methanolic potassium hydroxide was then added dropwise until the reaction mixture showed a slight pink color. The reaction mixture was then filtered to recover the desired product the potassium salt of 3,4,5,6-tetrabromophthalimide.

EXAMPLE 3

Preparation of an Isomeric Mixture of N-(Dichlorobenzoyl)-3,4,5,6-tetrabromophthalimides The potassium salt of 3,4,5,6-tetrabromophthalimide (0.162 moles) and dioxane (2000 ml) were charged into a glass reaction vessel equipped with a mechanical stirrer, thermometer and reflux condenser. An isomeric mixture of dichlorobenzoyl chloride (34 grams; 0.162 mole) containing 65.0 percent of the 2,5- isomer, 14.0 percent of the 2,3- isomer, 13.0 percent of the 3,4- isomer and 3.6 percent of the 3,5- isomer was then added dropwise to the reaction mixture with stirring at a temperature of 30° to 36°C over a period of about 75 minutes. After the addition was completed the reaction mixture was heated at reflux for a period of about 1 hour. The reaction mixture was then filtered while hot and the filtrate was stripped of solvent under reduced pressure to yield a solid. This solid was combined with 100 ml of dioxane and the mixture was heated to boiling, was filtered and the filtrate stripped of dioxane to yield 25 grams of the desired product, an isomeric mixture of N-(dichlorobenzoyl)-3,4,5,6-tetrabromophthalimides, as a yellow solid.

EXAMPLE 4

Preparation of 3,4,5,6-Tetrachlorophthalimide 3,4,5,6-Tetrachlorophthalic anhydride (0.30 mole) is charged into a glass reaction vessel. Concentrated ammonium hydroxide (280 ml) is incrementally added at room temperature with stirring. After the addition is completed the reaction slurry is heated with stirring for a period sufficient to evaporate most of the water present in the reaction mixture. The remaining solid is then dried in a forced air oven and is recrystallized. The recrystallized product is washed with acetone, filtered and dried to yield the desired product 3,4,5,6-tetrachlorophthalimide.

EXAMPLE 5

Preparation of the Potassium Salt of 3,4,5,6-Tetrachlorophthalimide

Anhydrous dioxane (2000 ml) is charged into a glass reaction vessel equipped with a mechanical stirrer and thermometer. The dioxane is heated to a temperature of about 95°C and 3,4,5,6-tetrachlorophthalimide (0.15 mole) is incrementally added with stirring. Potassium hydroxide (0.15 mole) dissolved in methanol is slowly added to the reaction mixture with heating and stirring. The reaction mixture is then cooled and a small amount of phenolphthalein indicator is added thereto. Additional methanolic potassium hydroxide is then added dropwise until the reaction mixture shows a slight pink color. The reaction mixture is then filtered to recover the desired product the potassium salt of 3,4,5,6-tetrachlorophthalimide.

EXAMPLE 6

Preparation of N-(2,4-Dichlorobenzyol)-3,4,5,6-tetrachlorophthalimide

The potassium salt of 3,4,5,6-tetrachlorophthalimide (0.10 mole) and dioxane (1200 ml) are charged into a glass reaction vessel equipped with a mechanical stirrer, thermometer and reflux condenser. 2,4-Dichlorobenzoyl chloride (0.10 mole) is then added dropwise, with stirring, to the reaction mixture at room temperature. After the addition is completed the reaction mixture is heated at reflux for a period of about 1 hour. After this time the reaction mixture is filtered and the filtrate is stripped of solvent to yield the desired product N-(2,4-dichlorobenzoyl)-3,4,5,6-tetrachlorophthalimide.

EXAMPLE 7

Preparation of N-(2,5-Dichlorobenzoyl)-3,4,5,6-tetrabromophthalimide

The potassium salt of 3,4,5,6-tetrabromophthalimide (0.10 mole) and dioxane (1200 ml) are charged into a glass reaction vessel equipped with a mechanical stirrer, thermometer and reflux condenser. 2,5-Dichlorobenzoyl chloride (0.10 mole) is then added dropwise, with stirring, to the reaction mixture at room temperature. After the addition is completed the reaction mixture is heated at reflux for a period of about 1 hour. After this time the reaction mixture is filtered and the filtrate is stripped of solvent to yield the desired product N-(2,5-dichlorobenzoyl)-3,4,5,6-tetrabromophthalimide.

EXAMPLE 8

Preparation of N-(2,3,5-Trichlorobenzoyl)-3,4,5,6-tetrabromophthalimide

The potassium salt of 3,4,5,6-tetrabromophthalimide (0.10 mole) and dioxane (1200 ml) are charged into a glass reaction vessel equipped with a mechanical stirrer, thermometer and reflux condenser. 2,3,5-Trichlorobenzoyl chloride (0.10 mole) is then added dropwise, with stirring, to the reaction mixture at room temperature. After the addition is completed the reaction mixture is heated at reflux for a period of about 1 hour. After this time the reaction mixture is filtered and the filtrate is stripped of solvent to yield the desired product N-(2,3,5-trichlorobenzoyl)-3,4,5,6-tetrabromophthalimide.

EXAMPLE 9

Preparation of N-(2,4,6-Tribromobenzoyl)-3,4,5,6-tetrachlorophthalimide

The potassium salt of 3,4,5,6-tetrachlorophthalimide (0.10 mole) and dioxane (1200 ml) are charged into a glass reaction vessel equipped with a mechanical stirrer, thermometer and reflux condenser. 2,4,6-Tribromobenzoyl chloride (0.10 mole) is then added dropwise, with stirring, to the reaction mixture at room temperature. After the addition is completed the reaction mixture is heated at reflux for a period of about 1 hour. After this time the reaction mixture is filtered and the filtrate is stripped of solvent to yield the desired product N-(2,4,6-tribromobenzoyl)-3,4,5,6-tetrachlorophthalimide.

EXAMPLE 10

Preparation of N-(Pentabromobenzoyl)-3,4,5,6-tetrabromophthalimide

The potassium salt of 3,4,5,6-tetrabromophthalimide (0.10 mole) and dioxane (1200 ml) are charged into a glass reaction vessel equipped with a mechanical stirrer, thermometer and reflux condenser. Pentabromobenzoyl chloride (0.10 mole) is then added dropwise, with stirring, to the reaction mixture at room temperature. After the addition is completed the reaction mixture is heated at reflux for a period of about 1 hour. After this time the reaction mixture is filtered and the filtrate is stripped of solvent to yield the desired product N-(pentabromobenzoyl)-3,4,5,6-tetrabromophthalimide.

EXAMPLE 11

Preparation of N-(Pentachlorobenzoyl)-3,4,5,6-tetrabromophthalimide

The potassium salt of 3,4,5,6-tetrabromophthalimide (0.10 mole) and dioxane (1200 ml) are charged into a glass reaction vessel equipped with a mechanical stirrer, thermometer and reflux condenser. Pentachlorobenzoyl chloride (0.10 mole) is then added dropwise, with stirring, to the reaction mixture at room temperature. After the addition is completed the reaction mixture is heated at reflux for a period of about 1 hour. After this time the reaction mixture is filtered and the filtrate is stripped of solvent to yield the desired product N-(pentachlorobenzoyl)-3,4,5,6-tetrabromophthalimide.

Organic polymeric compositions find wide application in the manufacture of molded and extruded articles as well as in paints, films, coatings and miscellaneous products. Since the great majority of organic polymeric compositions are highly flammable it is desirable to render these fire retardant. It has been found that the compound of this invention possesses the desirable property of rendering organic polymers fire retardant when incorporated therein.

Thus, a further embodiment of the present invention resides in fire retardant polymeric compositions comprising a combustible polymer and a fire retardant amount of a compound of this invention.

The compounds of this invention impart fire retardant properties to combustible polymers by forming intimate admixtures therewith. These admixtures can be readily prepared by one of several methods well known in the art. For example the compounds can be admixed into the combustible polymer while the latter is dissolved in a suitable solvent. This procedure is especially useful when it is desired to incorporate the compound during the preparation of the polymer. The compounds of this invention can also be mixed with a combustible polymer in the molten state at a temperature that can range from the melting point of the polymer to a temperature just below the decomposition temperature of the polymer. Another method of forming an intimate admixture comprises dry blending the compounds with the polymer in the finely divided state. Subsequent molding or extrusion of this blend can then result in a substantially homogeneous composition.

The fire retardant polymeric compositions of the instant invention can contain a fire retarding amount of one or more compounds of this invention. A fire retarding amount of a compound can range from about 5 to about 50 weight percent of the total composition. The exact amount of compound employed will depend upon such factors as the degree of fire retardancy desired, the specific combustible polymer used, the end use of the resulting product and the like.

The compounds of this invention can impart fire retardant properties to a variety of combustible polymers. Exemplary of such polymers which can be used in admixture with the compounds to form the fire retardant polymeric compositions of this invention are the homopolymers and copolymers of unsaturated aliphatic, cycloaliphatic, and aromatic hydrocarbons, such as polyethylene, polypropylene, polybutene, ethylene propylene copolymers, copolymers of ethylene or propylene with other olefins, polybutadiene, polymers of butadiene, polyisoprene, polystyrene, polyvinylidene, and polymers of pentene, hexene, heptene, octene, 2-methylpropene-1, 3-methylbutene-1, 4-methylpentene-1, 4-methylhexene-1, 5-methylhexene-1, bicyclohexene (2.2.1), pentadiene, hexadiene, 2,3-dimethylbutadiene-1,3 2-methylpentadiene, vinylcyclohexene such as 4-vinylcyclohexene, cyclopentadiene, methylstyrene and the like. Other useful polymers include indene-coumarone resins, polymers of acrylate esters and polymers of methacrylate esters, acrylate and methacrylate resins such as ethyl acrylate, n-butyl methacrylate, isobutyl methacrylate, ethyl methacrylate, and methyl methacrylate, alkyd resins, hydrocarbon resins from petroleum, isobutylene resins, polyurethanes, polyester resins such as unsaturated polyesters of dibasic acids and dihydroxy compounds, polyester elastomers, saturated thermoplastic polyesters, polyisobutylene, rubbers such as natural rubber, synthetic polyisoprene, polybutadiene, cyclized rubber, butadiene-acrylonitrile rubber, butadiene-styrene rubber, butyl rubber, neoprene rubber, terpene resins, urea resins, vinyl resins such as poly(vinyl acetal), poly(vinyl acetate), vinyl alcohol-acetate copolymer, poly(vinyl alcohol), poly(vinyl alkyl ether), vinyl methyl ether-maleic anhydride copolymer, poly(vinyl butyral), vinyl chloride-acetate copolymer, poly(vinyl pyrrolidone), vinylidene chloride copolymers and the like. Additional useful polymers include nylon, diallyl phthalates and phthalate resins and polycarbonates.

The fire retardant compositions of this invention can also contain adjuvants which in conjunction with the compounds of this invention improve the fire retardancy of the composition and in some instances provide synergistic results not obtainable with the use of a compound alone. Such adjuvants can comprise antimony compounds such as antimony trioxide, zinc borate, lead arsenates such as $PbHAsO_4$ and the like. These adjuvants can comprise from about 1 to about 35% by weight of the total composition.

The effectiveness of the compounds of this invention as flame retardants was demonstrated in an experiment wherein fire retardant compositions comprising the product of Example 3 and various combustible polymers were subjected to a flammability test using the oxygen index method. The flammability test was carried out in accordance with the general procedures detailed in the ASTM D 2863-70 test method. This method provides a procedure for determining the relative flammability of plastics by measuring the minimum concentration of oxygen expressed as volume percent, in a slowly rising mixture of oxygen and nitrogen that will just support combustion. The results of this experiment are set forth in the following examples. In each of these examples the components were blended in the molten state using a Brabender Plasticorder.

| | Composition Parts by Weight | Oxygen Index Percent |
|---|---|---|
| Example 12 | | |
| Polypropylene | 100 | 22.0–22.5 |
| Product of Example 3 | 25 | |
| Example 13 | | |
| ABS* | 100 | 22.5 |
| Product of Example 3 | 20 | |
| Example 14 | | |
| ABS* | 100 | 25.5 |
| Product of Example 3 | 20 | |
| Antimony trioxide | 5 | |

*Terepolymer of acrylonitrile, butadiene and styrene

We claim:
1. A compound of the formula

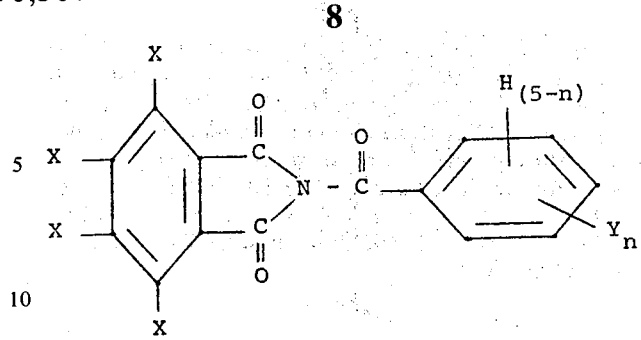

wherein X and Y are each chlorine or bromine and n is an integer from 2 to 5.

2. The compound of claim 1, N-(2,4-dichlorobenzoyl)-3,4,5,6-tetrachlorophthalimide.
3. The compound of claim 1, N-(2,5-dichlorobenzoyl)-3,4,5,6-tetrabromophthalimide.
4. The compound of claim 1, N-(2,3,5-trichlorobenzoyl)-3,4,5,6-tetrabromophthalimide.
5. The compound of claim 1, N-(2,4,6-tribromobenzoyl)-3,4,5,6-tetrachlorophthalimide.
6. The compound of claim 1, N-(pentabromobenzoyl)-3,4,5,6-tetrabromophthalimide.
7. A fire retardant polymeric composition comprising a combustible polymer and a fire retarding amount of the compound of claim 1.
8. The composition of claim 7 wherein the combustible polymer is polystyrene.
9. The composition of claim 7 wherein the combustible polymer is polyethylene.
10. The composition of claim 7 wherein the combustible polymer is a terepolymer of acrylonitrile, butadiene and styrene.
11. The composition of claim 7 wherein the combustible polymer is polypropylene.
12. The composition of claim 7 wherein the combustible polymer is a polyester.
13. The composition of claim 7 which contains from about 1 to about 35% by weight of an adjuvant selected from the group consisting of antimony trioxide, zinc borate and lead arsenate.

* * * * *